United States Patent [19]

George et al.

[11] Patent Number: 4,749,817

[45] Date of Patent: Jun. 7, 1988

[54] HYDRODECHLORINATION OF CHLORINATED BENZENES

[75] Inventors: Jacob George, Newark, Del.; Thomas A. Del Prato, Philadelphia, Pa.; Nicola A. Stufano, Jersey City, N.J.

[73] Assignee: Standard Chlorine of Delaware, Inc., Delaware City, Del.

[21] Appl. No.: 899,496

[22] Filed: Aug. 22, 1986

[51] Int. Cl.$^4$ .................. C07C 17/24; C07C 17/00
[52] U.S. Cl. .................................................. 570/204
[58] Field of Search ......................................... 570/204

[56] References Cited

U.S. PATENT DOCUMENTS

| | | | |
|---|---|---|---|
| 2,866,828 | 12/1958 | Crowder | 570/204 |
| 2,949,491 | 8/1960 | Rucker | 570/204 |
| 3,336,386 | 8/1967 | Dovell et al. | 502/223 |
| 3,595,931 | 7/1971 | Hay et al. | 570/204 |
| 3,892,818 | 7/1975 | Scharfe et al. | 585/469 |

*Primary Examiner*—J. E. Evans
*Attorney, Agent, or Firm*—Bert J. Lewen; Henry Sternberg

[57] ABSTRACT

Polychlorobenzenes are selectively dechlorinated to dichlorobenzenes and monochlorobenzene in the vapor phase in the presence of a sulfided palladium or platinum catalyst. The reaction may be carried out at a temperature of from 225° C. to 450° C., preferably at atmospheric pressure, with an equimolar ratio of hydrogen and polychlorobenzene, and a space velocity of 0.5 to 5 wt. feed/wt. catalyst-hour. Only small amounts of benzene are formed.

10 Claims, No Drawings

HYDRODECHLORINATION OF CHLORINATED BENZENES

Chlorinated benzenes are important chemical compounds used widely as raw materials for the production of agricultural chemicals, polymers, pharmaceuticals, etc. The most desirable products are monochlorobenzene, dichlorobenzenes and 1,2,4-trichlorobenzene. During production of these chemicals, other less desirable polychlorinated benzenes are also unavoidably produced. Such by-products include 1,2,3-trichlorobenzene, tetrachlorobenzenes, pentachlorobenzene and hexachlorobenzene, for which a limited commercial outlet presently exists.

It has long been desirable to upgrade these unwanted products and convert them to more valuable chlorobenzenes. One approach involves hydrodechlorination of polychlorobenzenes such as trichlorobenzenes and tetrachlorobenzenes to the more valuable lower chlorobenzenes such as monochlorobenzene and dichlorobenzenes. A variety of techniques are reported in the literature. For example, the dechlorination of a tetrachlorobenzene stream using a palladium-on-alumina catalyst is described in U.S. Pat. No. 2,826,617. U.S. Pat. No. 2,943,114 shows the use of a cuprous chloride on titanium dioxide for dechlorinating trichlorobenzene. The patent also suggests the use of copper chromite, nickel on kieselguhr, and platinum on alumina. Other references showing the dechlorination of trichlorobenzene include U.S. Pat. Nos. 2,886,605 and 2,866,828 using cupric chloride on activated alumina, nickel chromite suspended on calcium fluoride and platinum on carbon. Hexachlorobenzene is dechlorinated to pentachlorobenzene in U.S. Pat. No. 3,359,336 in the presence of hydrogen and steel wire gauze. Palladium supported on a polyamide is shown for dechlorinating chlorobenzene to benzene in Japanese Patent No. 79-59,233. The patent reports that palladium on alumina or palladium on carbon results in some hydrogenation of the ring.

The hydrodechlorination of chlorobenzene is described in Journal Chem. Soc., Perkin Trans., 2, 1975 (14), 1479-1482; Chem. Abstracts 84, 30070, using a platinum, rhodium or palladium supported on polyamide to yield 100% selectivity to benzene. In contrast, alumina based catalysts are shown to give a large portion of cyclohexane. Palladium is reported as the most active catalyst.

East German Patent No. 134,601 and U.S. Pat. No. 3,505,417 also show dechlorination reactions using platinum, cupric chloride and nickel on alumina and cupric oxide, chromium oxide, rhodium trichloride, platinum, and cobalt oxide in an aluminum trifluoride matrix. U.S. Pat. No. 3,697,608 shows a dechlorination process wherein the halocarbons are passed into a melt consisting of cuprous chloride, ferric chloride and potassium chloride.

Other patents showing dechlorination, but not of polychlorobenzenes, include German Offen. No. 2,258,769, which shows the dechlorination of chloroanilines over cupric chloride or silver chloride catalysts; French Demande No. 2,161,861, teaching the reaction of hydrogen with pentachlorophenol in the presence of alumina granules impregnated with cupric chloride; and Romanian Patent No. 64,264, showing the hydrodechlorination of 1,2,3,4,5,6-hexachloro cyclohexane over barium chloride, cupric chloride, zinc chloride, or ferrous chloride to give trichlorobenzene.

While the foregoing patents clearly show that hydrodechlorination in the vapor phase in the presence of a catalyst is feasible, there is no teaching of a method of converting trichlorobenzenes and tetrachlorobenzenes selectively to monochlorobenzene and dichlorobenzenes at high conversions. Naturally, this is necessary to provide a commercially viable process. Such process has become of even greater commercial importance in recent years since polychlorinated benzenes, often formed as unwanted by-products in related chemical reactions, are facing fewer and costlier methods of disposal. In addition, prior art processes also result in the formation of cyclohexane. This is particularly undesirable because cyclohexane has a boiling point close to benzene and is therefore difficult to separate therefrom.

BRIEF DESCRIPTION OF THE INVENTION

In accordance with the instant invention, it has now been discovered that polychlorobenzenes, particularly tri- and tetrachlorobenzenes, can be selectively hydrodechlorinated by means of a vapor phase reaction in the presence of a sulfided palladium or platinum catalyst. Surprisingly, the use of such catalysts prevents to a large extent the further hydrodechlorination of the mono- and dichlorobenzenes, thereby minimizing the formation of benzene and, more importantly, the formation of cyclohexane.

DETAILED DESCRIPTION OF THE INVENTION

The polychlorobenzenes used as the feedstock to the instant invention primarily include trichlorobenzenes and tetrachlorobenzenes. Generally speaking, the feedstock should contain at least 95% of chlorobenzenes having three or more chlorine atoms; however, the invention may also be applied to organic feedstocks containing only 75 or even 50% of the trichlorobenzenes and higher, where such compounds are found in admixture with lesser chlorinated homologues such as dichlorobenzenes. Similarly, the feedstock may contain up to about 5% of pentachlorobenzene and hexachlorobenzene.

In order to achieve the desired results of the invention, namely, a partial dechlorination, with the minimum formation of benzene, it is necessary that a sulfided palladium or platinum catalyst be used and that the reaction conditions be maintained within specified ranges. It will be understood that the optimum operating conditions will be a function of several variables, namely, the catalyst composition and level, the catalyst support, the temperature, the feed rate, the operating pressure, the hydrogen to chlorobenzene ratio and diluent concentration. For the particular system in question, those skilled in the art can readily determine the optimum based on the following criteria.

With regard to the catalyst, it is important that the metal be sulfided and remain sulfided during the course of the reaction. The exact mechanism by which the sulfur attaches to the metal is not fully understood. Though perhaps palladium or platinum sulfide, PdS or PtS, is formed, it is more likely that the metal and the sulfur interact through chemisorption and not ionic bonding. The preferred catalyst is the sulfided palladium.

In order to properly sulfide the palladium or platinum, a variety of non-poisoning sulfiding agents can be used. Examples are non-metallic sulfides such as carbon disulfide, sulfur monochloride, organic sulfur compounds such as thiophene. Sulfides of heavy metals, such as antimony sulfide and lead sulfide, are not effective because these compounds permanently poison the catalyst.

The amount of sulfiding is such that approximately one atom of sulfur is associated with each atom of the metal. Where the total sulfur fed is equal to the total palladium or platinum, an effective catalyst is obtained. Excess sulfur may be added, but this will generally not be advantageous. The metal may be "presulfided" before the commencement of the reaction or the sulfur-donating compound may be added along with the feedstock. During the course of the reaction, because of the presence of hydrogen in the feedstock, the catalyst may be depleted of the requisite amount of sulfur by the formation of hydrogen sulfide. This negative effect can be overcome by adding the sulfide donor periodically along with the feedstock during the course of the reaction. Effective methods of sulfiding the catalyst include "presulfiding" before the commencement of the reaction with hydrogen sulfide and adding periodically hydrogen sulfide along with the feedstock and the hydrogen during the reaction.

Advantageously, the sulfided catalyst is supported on a carrier, such as alumina, silica, zeolites or carbon. Preferably, the support is alumina. While the surface area of the support is not believed to be critical, with respect to alumina surface areas of 10 m$^2$/g to 300 m$^2$/g may be used, preferably from 40 m$^2$/g to 120 m$^2$/g.

The temperature of the reaction should, of course, be such that the feedstock is volatilized under the reaction pressure. Generally speaking, it is preferred to perform the reaction at nominal atmospheric pressure, since this is best from an economic standpoint; however, pressures in the range of 0.5 atm. to 10 atm. may be used, with the preferable range being from 1 to 3 atm.

Using a feedstock of trichlorobenzenes and tetrachlorobenzenes, the temperature range should broadly be from about 225° C. to 450° C., with 300° C. to 400° C. being preferred. The space velocity, expressed in weight of feed per weight of catalyst per hour, would broadly be between 0.5 to 5 wt. feed/wt. catalyst-hour. and preferably between 1 to 3 wt. feed/wt. catalyst-hour. The reaction conditions for hydrodechlorinating substituted chlorobenzenes, such as chlorotoluenes, are comparable to those used for the unsubstituted compounds. The optimum conditions can be readily determined by those skilled in the art.

The hydrogen to hydrocarbon ratio is important in determining the extent of the hydrodechlorination. Naturally, high hydrogen to hydrocarbon ratios will result in higher conversions and an increase in the sequential hydrodechlorination reactions and the formation of greater amounts of benzene. The exact ratio selected will be dependent on the temperature, but generally the mole ratio, defined as mole hydrogen per mole chlorobenzenes, will be from 0.2 to 2.0, preferably from 0.4 to 1.2, and most desirably from 0.5 to 1.0.

While not essential to the reaction, inert diluents may be added. For example, nitrogen may be present where the hydrogen used is from an ammonia splitter. In such instances, the nitrogen:hydrogen ratio on a volumetric basis would be approximately 1:3.

To illustrate more clearly the instant invention, a series of runs were performed in a 50 cc stainless steel reactor. The reactor is equipped with an inlet line at the bottom and an exit arm at the top which also serves as a charging port for the catalyst. The reactor is provided with a centerline thermowell which allows temperature monitoring of the catalyst bed by means of a travelling thermocouple. The reactor is immersed in a molten salt bath and the temperature is regulated by means of a temperature controller.

The feed system consists of two burettes. One burette (25 cc) is used to accurately monitor the feed rate while the other one (500 cc) is used as a feed reservoir. The feed is pumped through a Milton Roy pump and mixed with hydrogen. The collection systems consist of two glass condensers connected in series. The liquid is collected in a receiver situated at the bottom of the second condenser. The non-condensibles stream is passed through a caustic scrubber where HCl reacts with a 10% sodium hydroxide solution. Unconverted hydrogen is vented out of the system.

In a typical experiment, the salt temperature is brought to the desired temperature under a constant flow of nitrogen across the reactor. When the desired temperature is reached, nitrogen flow is stopped and hydrogen is then fed through the system. A bubblemeter is used to monitor the rate. When the desired rate is achieved, the feed pump is started. The system is allowed to reach steady state conditions, whereupon a run collection is initiated by recording the burette level and emptying the product collection vessel. The unit is operated unit about 50–70 grams of product have been collected. This amount is needed to ensure a satisfactory material balance. At the end of the collection, the burette level and run duration are recorded and the liquid product is transferred to a sample bottle for weighing and analysis.

In the following examples the productivity of each individual component is expressed in moles/hour. Similarly, the feed rate is expressed as throughput of each individual component in moles/hour. The results of the reaction are calculated as follows:

$$\% \text{ Conversion of tris} = \left[1 - \frac{\text{Moles/hr Tris + Tetras in Product}}{\text{Moles/hr Tris + Tetras in Feed}}\right] \times 100$$

$$\% \text{ Conversion of tetras} = \left[1 - \frac{\text{Moles/hr Tetras in Product}}{\text{Moles/hr Tetras in Feed}}\right] \times 100$$

$$\% \text{ Dechlorination} = \left[1 - \frac{\text{Total Cl atoms/hr in Product}}{\text{Total Cl atoms/hr in Feed}}\right] \times 100$$

$$\% \text{ Molar Selectivity to benzene} = \frac{\text{Moles/hr of Benzene in Product}}{\text{Moles/hr of Products}} \times 100$$

$$\% \text{ Molar Selectivity to } MCB = \frac{\text{Moles/hr of } MCB \text{ in Products}}{\text{Moles/hr of Products}} \times 100$$

$$\% \text{ Molar Selectivity to } ODCB = \frac{\text{Moles/hr of } ODCB \text{ in Product}}{\text{Moles/hr of Products}} \times 100$$

$$\% \text{ Molar Selectivity to } MDCB = \frac{\text{Moles/hr of } MDCB \text{ in Product}}{\text{Moles/hr of Products}} \times 100$$

$$\% \text{ Molar Selectivity to } PDCB = \frac{\text{Moles/hr of } PDCB \text{ in Product}}{\text{Moles/hr of Products}} \times 100$$

where Moles/hr of Products=Moles/hr(Benzene+MCB+ODCB+MDCB+PDCB)

EXAMPLE 1

A polychlorobenzene feed containing a mixture of trichlorobenzenes and tetrachlorobenzenes was passed through a reactor maintained at 300° C. and containing 48 grams of catalyst. The catalyst, 0.5% palladium on ⅛" alumina and having a surface area of 90 m²/g, was sulfided by the introduction of feed containing 500 ppm thiophene for a period of 6 hours. During that time hydrogen was continuously fed to the reactor at a rate such that the hydrogen to chlorobenzene molar ratio was maintained at about 0.70. The reaction was carried out for 6 hours during which time an average feed rate of 1.2 g/min was maintained. The results obtained from this example illustrate the decreased formation of benzene and the increased selectivity of the more valuable products such as chlorobenzene and dichlorobenzenes. The following table compares the results obtained with another run using non-sulfided catalyst of the same composition, same experimental conditions and the same feed.

|  | Feed Wt. % | Non-Sulfided Pd/Al$_2$O$_3$ | | Sulfided Pd/Al$_2$O$_3$ | |
| --- | --- | --- | --- | --- | --- |
|  |  | Product Wt. % | % Molar Selectivity | Product Wt. % | % Molar Selectivity |
| Benzene |  | 2.52 | 20.48 | 0.20 | 3.24 |
| MCB |  | 1.45 | 8.24 | 0.92 | 10.39 |
| 1,3 DCB |  | 1.75 | 7.57 | 1.78 | 15.38 |
| 1,4 DCB |  | 0.87 | 3.79 | 1.70 | 14.68 |
| 1,2 DCB |  | 13.84 | 59.92 | 6.52 | 56.31 |
| 1,2,4 TCB | 45.68 | 29.18 |  | 42.80 |  |
| 1,2,3 TCB | 15.47 | 19.48 |  | 19.66 |  |
| 1,2,4,5 TECB | 1.68 | 1.41 |  | 1.17 |  |
| 1,2,3,4 TECB | 37.17 | 29.50 |  | 25.25 |  |
| TOTAL | 100.00 | 100.00 | 100.00 | 100.00 | 100.00 |

EXAMPLE 2

This example illustrates a process in which a different sulfur compound was used to successfully sulfide the catalyst. 58.7 g of the catalyst (0.5% palladium on ⅛" alumina with a surface area of 90m²/g) was charged into the reactor and kept at 300° C. under a nitrogen flow. A mixture of trichlorobenzenes and tetrachlorobenzenes containing 2000 ppm of carbon disulfide was fed into the reactor for 5 hours under nitrogen flow. When the sulfiding step was completed, addition of the CS$_2$ spiked material was discontinued and the reaction cycle was initiated by feeding a mixture of tri- and tetra-chlorobenzenes and hydrogen. The molar ratio of hydrogen to chlorobenzene was kept at 0.75 with a chlorobenzene feed rate of 1.59 g/min. The composition of the product obtained and the feed used for this example are given in the following table.

|  | Feed Wt. % | Product Wt. % | Product % Molar Selectivity |
| --- | --- | --- | --- |
| Benzene |  | 0.46 | 4.21 |
| MCB |  | 1.99 | 12.65 |
| 1,3 DCB |  | 3.28 | 15.97 |
| 1,4 DCB |  | 2.76 | 13.43 |
| 1,2 DCB |  | 11.04 | 53.74 |
| 1,2,4 TCB | 45.02 | 36.00 |  |
| 1,2,3 TCB | 15.64 | 20.26 |  |
| 1,2,4,5 TECB | 2.11 | 0.98 |  |
| 1,2,3,4 TECB | 37.23 | 23.23 |  |
| TOTAL | 100.00 | 100.00 | 100.00 |

The extent of dehalogenation during this example was 13.18% and the conversion of the tetrachlorobenzenes was 41.02%. The total dehalogenation was slightly lowered when compared to the unsulfided catalyst; however, the tetrachlorobenzene conversion was enhanced, which resulted in a better selectivity to the desired products. After 110 hours on stream, the sulfiding effect was diminished. Thereafter, a second sulfidation was carried out as described above and the experiment was continued for another 135 hours without changing the product profile. After 15 hours into the cycle, when an unsulfided palladium catalyst was employed, the benzene/monochlorobenzene ratio was about 1.6, while, with the sulfided palladium, the ratio was only 0.375. The sulfiding somewhat shortened the reaction cycle of the catalyst and increased the regeneration cycle; however, no permanent adverse effects on the catalyst were noticed during the 245 hours of operation.

EXAMPLE 3

Presulfided palladium on alumina (0.5% palladium on ⅛" alumina having a surface area 90 m²/g) obtained from Alfa Chemicals was used for this example. The object of the study was to determine the long term efficacy of the process of the invention by completing 38 cycles of operation over a period of 725 hours. A mixture of trichloro- and tetrachlorobenzenes having the same composition as that employed in Example 2 was fed to the reactor which was charged with 61 grams of the presulfided palladium and maintained at 300° C. Hydrogen at a mole ratio of hydrogen to chlorobenzene of about 0.75 was fed to the reactor continuously. At the end of each cycle the catalyst was regenerated by the controlled introduction therethrough of a slow stream of air for 2 to 4 hours. At the end of the regeneration cycle the reactor was flushed with nitrogen and a new reaction cycle was started.

The composition of the product collected from cycle 1 during this example along with the molar selectivity is given in the following table:

|  | Feed Wt. % | Product | |
| --- | --- | --- | --- |
|  |  | Wt. % | % Molar Selectivity |
| Benzene |  | 0.71 | 6.49 |
| MCB |  | 1.82 | 11.55 |
| 1,3 DCB |  | 3.03 | 14.72 |
| 1,4 DCB |  | 2.16 | 10.49 |
| 1,2 DCB |  | 11.68 | 56.75 |
| 1,2,4 TCB | 44.86 | 34.53 |  |
| 1,2,3 TCB | 15.12 | 19.40 |  |
| 1,2,4,5 TECB | 2.13 | 1.16 |  |
| 1,2,3,4 TECB | 37.89 | 25.51 |  |
| TOTAL | 100.00 | 100.00 | 100.00 |

The extent of dechlorination during this cycle was 13.39% with 38.70% tetrachlorobenzenes conversion. Hydrogen conversion initially was 100%. It gradually dropped to 75% after 20 hours. The effect of sulfiding the catlayst is again demonstrated when the product distribution and the molar selectivity of the products obtained in this example are compared to a non-sulfided catalyst results obtained under the similar experimental conditions shown in Example 1. The effect of sulfur was the suppression of benzene formation, with near-maximum consumption of hydrogen. This effect was particularly evident for the first 300 hours of operation.

EXAMPLE 4

This example illustrates a process of sulfiding the catalyst using sulfur monochloride and resulfiding the catalyst when the sulfiding effect diminishes after several cycles of operation. 60 g of 0.5% palladium on ⅛" alumina pellets having a surface area of 90 m²/g was charged into a 75 cc reactor maintained at 300° C. and kept under nitrogen purge. Enough sulfur monochloride was dissolved in 250 ml of trichloro and tetrachlorobenzene mixture such that one mole of sulfur per mole of palladium is fed over the catalyst. The bath temperature was reduced to 200° C. so that the chlorobenzene mixture could be fed below the boiling point. Once the bath temperature was stabilized, the chlorobenzene mixture containing the sulfur monochloride was fed to the reactor at a rate of 1 ml/min under nitrogen flow. Thereafter, the catalyst bed was left filled with the feed containing sulfur monochloride for an additional 2 hours. Once the sulfiding step was completed, the catalyst was regenerated and a reaction cycle was initiated as described in the previous examples. The composition of the feed for dechlorination and the product obtained are shown in the following table:

|  | Feed Wt. % | Product Wt. % | % Molar Selectivity |
| --- | --- | --- | --- |
| Benzene |  | 0.84 | 6.51 |
| MCB |  | 3.28 | 18.10 |
| 1,3 DCB |  | 2.86 | 12.10 |
| 1,4 DCB |  | 2.39 | 10.02 |
| 1,2 DCB |  | 12.49 | 53.27 |
| 1,2,4 TCB | 45.52 | 33.73 |  |
| 1,2,3 TCB | 15.07 | 20.86 |  |
| 1,2,4,5 TECB | 1.00 | 0.44 |  |
| 1,2,3,4 TECB | 38.41 | 23.11 |  |
| TOTAL | 100.00 | 100.00 | 100.00 |

The extent of dechlorination in this example was 18.35% with 49.74% tetra-conversion. After 322 hours on stream the sulfiding effect was slightly reduced and the benzene/MCB ratio rose from 0.36 to 1.08.

In order to obtain the most desirable product profile throughout, the catalyst was then subjected to another sulfidation step as explained earlier in this example. After the resulfidation step, the activity of the catalyst was regained and the benzene/MCB ratio was found to be 0.30.

EXAMPLE 5

This example demonstrates the advantage of using sulfided catalyst to reduce the cyclohexane formation during hydrodehalogenation reaction. The catalyst was 0.5% palladium on ⅛" alumina with a surface area of 90 m²/g, the feed rate was 1.59 g/min, and the mole ratio of hydrogen to chlorobenzene was 0.75. The catalyst was sulfided using sulfur monochloride as described in Example 4. Product analysis from the experimental runs revealed that sulfiding the catalyst reduced the formation of cyclohexane. Under the same conditions of operation prior to sulfidation of the catalyst, the benzene/cyclohexane mole ratio in the dehalogenated product was found to be 10:1. One such cycle contained 894 ppm cyclohexane, corresponding to a benzene/cyclohexane ratio of 10.5:1 with 50% tetrachlorobenzene conversion. During the first cycle subsequent to sulfidation, less than 5 ppm of cyclohexane was present. This corresponds to a benzene/cyclohexane ratio of about 6000:1. After 250 hours of operation, the cyclohexane formation increased to 130 ppm, yielding a ratio of 50:1, which is still superior to the non-sulfided case. Upon resulfiding the catalyst, the cyclohexane formation was again reduced to 2.6 ppm, corresponding to a mole ratio of 6340:1.

EXAMPLE 6

This example shows the use of platinum as a dehalogenation catalyst and the efficacy of sulfiding such catalyst to improve the product selectivity. 58.7 g of the catalyst (0.5% platinum on ⅛" alumina with a surface area of 90 m²/g) was charged in to a 75 cc reactor and maintained at 300° C. under nitrogen flow. The catalyst was then activated by the controlled introduction of air. Once the activation cycle (1 hour) was completed, the reactor was purged with nitrogen and the normal reaction cycle was initiated by feeding a mixture of trichloro- and tetrachlorobenzenes. Hydrogen at a mole ratio of hydrogen to chlorobenzene of about 0.75 was fed to the reactor continuously. At the end of normal dehalogenation cycle, the catalyst was sulfided using sulfur monochloride ($S_2Cl_2$) as described in Example 4. Following the sulfidation step, the catalyst was regenerated and the dehalogenation operation was initiated. Composition of the feed and the product collected before and after sulfidiation are given below.

|  |  | 6th Hour Product | | | |
| --- | --- | --- | --- | --- | --- |
|  |  | Non-Sulfided Pt | | Sulfided Pt | |
|  | Feed Wt. % | Wt. % | Selectivity Mol % | Wt. % | Selectivity Mol % |
| Benzene |  | 0.52 | 7.30 | 0.20 | 2.50 |
| Chlorobenzene |  | 0.93 | 9.06 | 1.39 | 12.07 |
| 1,3 DCB |  | 1.24 | 9.24 | 1.74 | 11.56 |
| 1,4 DCB |  | 0.81 | 6.04 | 1.57 | 10.43 |
| 1,2 DCB |  | 9.71 | 68.38 | 9.55 | 63.44 |
| 1,2,4 TCB | 45.52 | 36.70 |  | 35.07 |  |
| 1,2,3 TCB | 15.07 | 18.62 |  | 21.42 |  |
| 1,2,4,5 TeCB | 1.00 | 0.95 |  | 0.40 |  |
| 1,2,3,4 TeCB | 38.41 | 31.06 |  | 28.48 |  |
| TOTAL | 100.00 | 100.00 | 100.00 | 100.00 | 100.00 |

The tetrachlorobenzene conversion in the above examples was 20.6% (0.91 benzene/MCB ratio) and 26.72% (0.21 benzene/MCB ratio) for non-sulfided and sulfided platinum, respectively.

When comparing the non-sulfided forms of platinum and palladium, it was found that platinum was not as effective as palladium for hydrodehalogenation. Tetrachlorobenzene conversions of over 40% are obtainable with Pt/alumina as with Pd/alumina. The drawback with Pt/alumina was the shorter effective cycle life. For the first 10 hours of the cycle the product profile matched that of Pd/alumina but thereafter there was a sharp decrease in the activity. After 24 hours, while tetrachlorobenzene conversions were still about 40% for Pd/alumina, Pt/alumina showed only 15% or less.

Upon sulfiding, the platinum catalyst exhibited the same characteristics of sulfided palladium catalyst. The benzene-monochlorobenzene ratio was reduced from 1.0 to 0.30 while maintaining the same conversion levels. The amount of cyclohexane in the product was found to be about 30 ppm, which corresponds to a benzene/cyclohexane mol ratio of 620:1, while the non-sulfided platinum showed a ratio of about 10:1.

EXAMPLE 7

This example shows the efficacy of utilizing hydrogen sulfide as the sulfiding agent prior to hydrodechlorination. 60 grams of 0.5% palladium on ⅛" alumina having a surface area of 90 m²/g was charged into a 75 cc reactor and maintained at 300° C. under nitrogen purge. Prior to sulfiding the catalyst, a hydrodechlorination cycle was performed by feeding a mixture of tri- and tetrachlorobenzene at a rate of 1.5 g/min. The hydrogen to chlorobenzene ratio was kept at 0.75. Upon completion of the dechlorination cycle, the catalyst bed was purged with nitrogen and then regenerated with air for 1 hour. Following the regeneration cycle, the catalyst was sulfided by passing hydrogen sulfide over the bed which was maintained at 300° C. Hydrogen sulfide treatment was continued for 5 min. During that time the total amount of sulfur fed into the catalyst bed was slightly over 1 mole per mole of palladium. After the completion of the sulfidation procedure, the catalyst was regenerate and a hydrodechlorination cycle was repeated as described above.

The results obtained during the hydrodechlorination cycles, before and after sulfidation, are given in the following table.

|  | Feed Wt. % | Product Non-Sulfided |  | Sulfided |  |
|---|---|---|---|---|---|
|  |  | Wt. % | Selectivity Mol % | Wt. % | Selectivity Mol % |
| Benzene |  | 7.81 | 28.13 | 3.41 | 13.58 |
| MCB |  | 7.44 | 18.60 | 7.24 | 20.01 |
| 1,3 DCB |  | 3.83 | 7.33 | 5.85 | 12.37 |
| 1,4 DCB |  | 2.21 | 4.23 | 4.80 | 10.15 |
| 1,2 DCB |  | 21.80 | 41.71 | 20.75 | 43.89 |
| 1,2,4 TCB | 45.06 | 21.18 |  | 28.51 |  |
| 1,2,3 TCB | 15.98 | 19.16 |  | 14.66 |  |
| 1,2,4,5 TECB | 1.05 | 0.43 |  | 0.40 |  |
| 1,2,3,4 TECB | 37.91 | 16.14 |  | 14.38 |  |
| TOTAL | 100.00 | 100.00 | 100.00 | 100.00 | 100.00 |

The tetrachlorobenzene conversion prior to sulfiding was 57.5% with a benzene/MCB ratio of 1.51. After sulfiding, conversion was increased to 62.1% with a reduced benzene/MCB ratio of 0.68. The cyclohexane formed during the reaction was also reduced by sulfidation. The dehalogenated product from the non-sulfided palladium run showed the presence of 4930 ppm cyclohexane while the sulfided catalyst produced only 20 ppm, corresponding to a benzene/cyclohexane ratio of 15 and 1176, respectively.

EXAMPLE 8

This example shows the utility of sulfided noble metals as a dehalogenation catalyst for substituted chlorobenzenes. The catalyst used was 0.5% palladium on ⅛" alumina. 2,4-Dichlorotoluene was used as the feed and the feed rate was maintained at about 1.25 g/min. The dehalogenation reaction catalysed by non-sulfided palladium at a temperature of 300° C. was found to be very vigorous. Up to 81% toluene was formed during such dehalogenation, yielding a mole ratio of toluene-chlorotoluene of 4.24. When the dehalogenation was catalysed by a sulfided palladium, the reaction rate was reduced considerably and the selectivity to chlorotoluene was improved. Only 41% toluene was found in the dehalogenated product which corresponded to a toluene/chlorotoluene mole ratio of 1.19. Thus sulfided palladium was found to be effective in improving selectivity to substituted chlorobenzene.

COMPARATIVE EXAMPLE

The palladium catalyst described in the previous example was sulfided using antimony sulfide. 59 g of the catalyst was charged into a 75 cc reactor. 150 mg of antimony sulfide was placed in the bottom of the reactor as the sulfur source. The catalyst was regenerated and the normal dechlorination was carried out using a mixture of trichloro- and tetrachlorobenzene. During the first reaction cycle the catalyst performed satisfactorily; however, the activity was reduced rapidly in the following cycles. The rapid drop in the dehalogenation rate and the tetra-conversion indicated that the catalyst was poisoned and the deactivation was found to be irreversible.

|  | 1st Cycle |  | 2nd Cycle |  |
|---|---|---|---|---|
|  | Wt. % | Selectivity | Wt. % | Selectivity |
| Benzene |  | 0.61 | 7.37 | 0.22 | 5.18 |
| MCB |  | 1.88 | 15.76 | 0.53 | 8.67 |
| 1,3 DCB |  | 2.42 | 15.53 | 1.10 | 13.77 |
| 1,4 DCB |  | 2.04 | 13.09 | .73 | 9.14 |
| 1,2 DCB |  | 7.52 | 48.25 | 5.05 | 63.24 |
| 1,2,4 DCB | 46.70 | 37.68 |  | 40.71 |  |
| 1,2,3 DCB | 15.14 | 17.08 |  | 16.95 |  |
| 1,2,4,5 TECB | 1.97 | 1.26 |  | 1.41 |  |
| 1,2,3,4 TECB | 36.19 | 29.51 |  | 33.30 |  |
| % Dehalogenation |  | 10.00 |  | 4.85 |  |
| % TECB Conversion |  | 24.35 |  | 10.19 |  |

We claim:

1. A process for the partial hydrodechlorination of chlorinated benzenes having at least two chlorine atoms attached to the benzene ring which comprises reacting hydrogen and a chlorinated benzene in the vapor phase in the presence of a sulfided palladium or platinum catalyst at a temperature between 225° and 450° C., a pressure from 0.5 to 10 atm., a space velocity from 0.5 to 5 wt. feed/wt. catalyst-hour, and a molar ratio of hydrogen to chlorinated benzene from 0.2 to 2.0 and effecting said dechlorination so as to maximize mono-dechlorination and minimize benzene formation.

2. The process of claim 1 wherein the polychlorobenzene is selected from tetrachlorobenzenes, trichlorobenzenes and mixtures thereof, and the reaction products are predominantly monochlorobenzene and dichlorobenzenes.

3. The process of claim 1 wherein the sulfided palladium catalyst is supported on alumina, silica, a zeolite, or carbon.

4. The process of claim 3 wherein the support is alumina and the surface area is from 10 to 300 m²/g.

5. The process of claim 3 wherein from 0.05 to 5 wt. % of catalyst is present, based on the weight of support.

6. The process of claim 1 wherein the catalyst is sulfided palladium.

7. The process of claim 1 wherein the catalyst is sulfided with a sulfiding agent added to the feedstock during at least a part of the reaction period.

8. The process of claim 1 wherein an inert diluent is present.

9. The process of claim 1 wherein the catalyst is sulfided with a non-metallic sulfide.

10. The process of claim 1 wherein the catalyst is sulfided with hydrogen sulfide, sulfur monochloride or an organic sulfide.

* * * * *